US008082192B2

(12) United States Patent
Nycz et al.

(10) Patent No.: US 8,082,192 B2
(45) Date of Patent: Dec. 20, 2011

(54) AUTOMATED PASS-THROUGH SURGICAL INSTRUMENT TRAY READER

(75) Inventors: Jeffrey H Nycz, Warsaw, IN (US); Steven M Tethrake, Collierville, TN (US); Mark J Pelo, Macy, IN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 12/618,190

(22) Filed: Nov. 13, 2009

(65) Prior Publication Data
US 2010/0108761 A1    May 6, 2010

Related U.S. Application Data

(62) Division of application No. 10/924,897, filed on Aug. 25, 2004, now Pat. No. 7,644,016.

(51) Int. Cl.
G06Q 10/00 (2006.01)
A01K 5/02 (2006.01)
G08C 19/04 (2006.01)
(52) U.S. Cl. ................ 705/28; 705/29; 340/870.11
(58) Field of Classification Search ............... None
See application file for complete search history.

(56) References Cited

U.S. PATENT DOCUMENTS

| 4,075,632 A | 2/1978 | Baldwin |
| 4,360,801 A | 11/1982 | Duhame |
| 4,390,880 A | 6/1983 | Henoch |
| 4,688,026 A | 8/1987 | Scribner |
| 4,739,328 A | 4/1988 | Koelle |
| 5,030,807 A | 7/1991 | Landt |
| 5,621,199 A | 4/1997 | Calari |
| 5,923,001 A | 7/1999 | Morris |
| 5,963,134 A | 10/1999 | Bowers |
| 6,158,437 A | 12/2000 | Vagley |
| 6,164,738 A | 12/2000 | Dane |
| 6,318,636 B1 | 11/2001 | Reynolds |
| 6,405,863 B1 | 6/2002 | Dhindsa |
| 6,415,978 B1 | 7/2002 | McAllister |
| 6,426,041 B1 | 7/2002 | Smith |
| 6,429,776 B1 | 8/2002 | Alicot |
| 6,480,101 B1 | 11/2002 | Kelly |
| 6,523,752 B2 | 2/2003 | Nishitani |
| 6,646,241 B1 | 11/2003 | Varma |
| 6,669,089 B2 | 12/2003 | Cybulski |
| 6,777,623 B2 | 8/2004 | Ballard |
| 6,825,766 B2 | 11/2004 | Hewitt |
| 6,853,303 B2 | 2/2005 | Chen |
| 6,861,954 B2 | 3/2005 | Levin |

(Continued)

OTHER PUBLICATIONS

Presentation by Innovision Research and Technology, PLC at the "RFID in Healthcare" conference in Washington, DC on Dec. 2 and Dec. 3, 2003.

(Continued)

Primary Examiner — Faris Almatrahi

(57) ABSTRACT

An apparatus and method for interrogating and automatically identifying a radio-frequency tagged surgical instrument tray and its contents of RFID-tagged surgical instruments are disclosed. The surgical instrument tray and its contents come into contact with an RF signal transmitted by the RFID reader, and as a result, the RFID tags affixed on the instrument tray and the surgical instruments respond by transmitting back to the RFID reader data pertaining to the history of the surgical instruments. A data terminal, which is connected to the RFID reader, may contain data pertaining to the radio frequency tagged surgical instruments during packaging, and during the return of the surgical instrument trays to the packager, identifies the surgical instruments.

5 Claims, 6 Drawing Sheets

U.S. PATENT DOCUMENTS

| | | | |
|---|---|---|---|
| 6,866,147 B2 | 3/2005 | Barwick | |
| 7,268,684 B2* | 9/2007 | Tethrake et al. | 340/572.1 |
| 2002/0063622 A1 | 5/2002 | Armstrong | |
| 2002/0105424 A1 | 8/2002 | Alicot | |
| 2002/0143320 A1 | 10/2002 | Levin | |
| 2002/0188259 A1 | 12/2002 | Hickle | |
| 2003/0052788 A1 | 3/2003 | Kwong-Tai Chung | |
| 2003/0164401 A1 | 9/2003 | Andreasson | |
| 2003/0174099 A1 | 9/2003 | Bauer | |
| 2003/0178488 A1 | 9/2003 | Southard | |
| 2003/0189094 A1 | 10/2003 | Trabitz | |
| 2003/0196837 A1 | 10/2003 | Ballard | |
| 2004/0008123 A1* | 1/2004 | Carrender et al. | 340/825.49 |
| 2004/0022227 A1 | 2/2004 | ynch | |
| 2004/0031626 A1 | 2/2004 | Morris | |
| 2004/0069851 A1 | 4/2004 | Grunes | |
| 2004/0100384 A1 | 5/2004 | Chen | |
| 2004/0100415 A1* | 5/2004 | Veitch et al. | 343/850 |
| 2004/0160233 A1 | 8/2004 | Forster | |
| 2004/0174244 A1 | 9/2004 | Eidemiller | |
| 2004/0174261 A1 | 9/2004 | Volpi | |
| 2004/0220602 A1 | 11/2004 | Deng | |
| 2004/0220860 A1 | 11/2004 | Persky | |
| 2004/0250819 A1 | 12/2004 | Blair | |
| 2004/0267297 A1 | 12/2004 | Malackowski | |
| 2005/0003757 A1 | 1/2005 | Anderson | |
| 2005/0012617 A1 | 1/2005 | DiSilvestro | |

OTHER PUBLICATIONS (http://rfidjournal.com/article/view/112) RFID Journal, Can RFID Cure Healthcare's IIIs?, Nov. 12, 2002.

(http://usatoday.printthis.clickability.com/pt/cpt?action=cpt&expire-&urlID=8067862&fb= ...) Svensson, Peter "Conductive ink advances electronics," USATODAY.COM—(New York) pp. 1-3.

(http://www.eetimes.com/showPressRelease.jhtml?articleID=57907) EE Times (www.eetimes.com) "T-Ink™ to Be Featured" Feb. 14, 2003, pp. 1-2.

(http://americanprinter.com/microsites/magazinearticle.asp?mode=print&magazinearticleid...) American printer (www.americanprinter.com) "Tracking RFID Progress" Jan. 1, 2004, pp. 1-3.

(http://pffc-online.com/microsites/newsarticle.asp?mode=print&newsarticleid=2708965&re) Byrd-Thompson, Nsenga, (PFFC) Paper Film & Foil Converter (www.pffc-online.com), "RFID and Conductive Inks: What You need to Know" pp. 1-3.

* cited by examiner

FIG. 6

AUTOMATED PASS-THROUGH SURGICAL INSTRUMENT TRAY READER

This application is a divisional of co-pending U.S. application Ser. No. 10/924,897, filed Aug. 25, 2004, the entire contents of which are hereby incorporated by reference.

FIELD OF THE INVENTION

The invention generally relates to a method and apparatus for identifying instruments using radio frequency identification (RFID) techniques, and more particularly to a method and apparatus for implementing a reader for tracking, inspecting and verifying inbound and outbound surgical instrument trays, kits, and other instruments, to facilitate tracking and inventory management of surgical instruments and surgical instrument trays and kits over their useful life cycle.

BACKGROUND OF THE INVENTION

Most of the existing radio frequency readers of RFID-tagged items are employed in a wide variety of identification systems such as asset tracking of goods in department stores, books in libraries, inventory management, asset tracking, matching baggage to passengers in commercial aircrafts, monitoring work in progress, customer identification, delivery control, and delivery of goods such as automatic dispensing of gasoline at gas stations where a reader interrogates a tag on the vehicle, verifies the data received from the RFID tag, and authorizes the dispensing of fuel.

Surgical instrument storage and sterilization systems are known. These systems, known as surgical instrument trays or surgical instrument kits, typically consist of metal or plastic trays that hold a variety of general purpose and/or procedure specific surgical instruments such as forceps, scissors, clamps, retractors, scalpels, etc. These trays are brought into the operating room (OR) when preparing for surgery, and also are used as a means to organize, transport and store surgical instruments in a medical facility. It is desirable to be able to identify and inventory the medical surgical instruments to facilitate, repair, and replace them, should they become broken or worn. Tracking and managing surgical instruments used by hospitals is paramount to the efficiency and safety of the use of such surgical instruments, as well as other hand held medical or surgical instruments.

Due to advances in medical technology that have increased the number of surgical instruments now in use and due to the constant pressure in the health care industry to reduce operating costs, it has become necessary to manage and track these instruments more quickly and efficiently. One advancement towards this end has been the creation of surgical instrument trays that employ various techniques for controlling the arrangement of instruments on the tray so that any missing instruments can be identified quickly. One such method is disclosed in U.S. Pat. No. 6,158,437, which uses a combination of instrument identifying indicia including a plurality of graphical indicia that represent an outline of the basic shape of each instrument, as well as a terse written description of the instrument to identify the correct placement of specific surgical instruments on a tray. Another such method is disclosed in U.S. Pat. No. 6,4265,041, which utilizes a plurality of recessed sections of applicable shape and size distributed on the work surface of the tray to accommodate specific instruments. Upon extraction from the tray, the instruments are in ready position to be relayed to the person performing the operation. U.S. Pat. Nos. 6,158,437 and 6,4265,041 are hereby incorporated by reference in their entireties. Through implementation of the teachings of these patents, a person can visually inspect a surgical instrument tray and make a determination as to whether any instruments are missing or misplaced.

Another function provided by surgical trays is to facilitate group sterilization. Sterilization is of paramount importance in a surgical setting such as a hospital to prevent potentially deadly infections to patients undergoing surgery. Prior to every surgical procedure, all surgical instruments and trays must be sterilized. Also, following each surgical procedure, all instruments on a given tray, if not wrapped separately, whether soiled or not, must be re-sterilized before subsequent usage. In order to increase the speed and efficiency of sterilization, entire surgical trays containing several instruments often are placed in a sterilization chamber at once. The sterilization chamber may provide any combination of heat, pressure, and/or fluid or vaporous sterilant to the trays and all the instruments contained therein. Sterilization techniques are ubiquitously well known in the art. Thus, a detailed discussion of them has been intentionally omitted.

Over time, and through ordinary usage, as well as due to the sterilization process, surgical instruments suffer wear and tear and eventually reach the end of their life cycle. Thus, it has become necessary to periodically inspect and maintain records on usage of surgical instruments so that they can be replaced as necessary. Also, due to the fact that they are constantly moved from the operating room to sterilization, to storage, and back to the operating room, various instruments on a given tray may become lost. Because certain instruments are so specialized that there are no functional substitutes, it also has become necessary to regularly inspect trays for any missing instruments and to readily identify specific instruments that are missing. Existing methods for performing these necessary functions are overly reliant on costly human interpretation. Also, in some cases, a skilled technician may be required to identify missing instruments.

Several methods currently exist for tracking and providing information about items that may be useful for tracking surgical instruments and trays. For example, in retail and manufacturing applications, inventory items typically carry printed labels providing information such as serial numbers, price, weight, manufacturing or use dates, and size. Usually, these labels are not machine readable, but rather require human interpretation. Another method for tracking and providing information about items that ameliorates some of the short comings of printed labels is bar code labeling. Bar code labels are characterized by a pattern of vertically oriented machine readable variable width bars that, when illuminated with a bar code scanner, create a reflection pattern that translates into a unique series of numbers. The series of numbers must then be correlated to product descriptions in a relational database in communication with the bar code scanner for purposes of identification, price checking, and inventory management.

Bar code labels have received widespread use from product tracking in the package delivery business, to physical inventory tracking and even point-of-sale terminals. In some respects, due to their machine readable nature, bar code labels represent a significant improvement over printed labels. Also, they are relatively cheap and easy to generate with a printer. There are some limitations to bar codes, however, that limit their application to surgical instruments and trays. Bar codes are limited in size by resolution limitations of bar code scanners, and the amount of information that the symbols can contain is limited by the physical space constraints of the label. Therefore, some objects may be unable to accommodate bar code labels because of their size and physical configuration. In the field of surgical instruments, this may preclude bar code labels from some smaller or non-geometrically shaped instruments. In addition, labels only store a number that is meaningless until associated with a database.

Another limitation of bar code readers is that they require line of sight in order to read the reflection pattern from a bar code. One problem is that as labels become worn or damaged, they can no longer be read with the bar code scanner. This is particularly likely in the field of surgical instrument trays because of the harsh conditions the labels must undergo during sterilization. Also, because a person operating the bar code scanner must physically orient either the scanner or the product to achieve line of sight on each item being scanned, items must be scanned one at a time resulting in prolonged scan time. In addition, because bar code scanning requires the operator to handle each instrument in order to scan it, a potential safety problem is created. Soiled instruments pose a biohazard because they may have come in contact with bodily fluids, and often have sharp edges. After the instruments have been sterilized, they should not be touched again until surgery to prevent contamination. Therefore, direct human contact either pre or post sterilization may be problematic. Another limitation of bar code labels is that they are static. Updating the information in these machine-readable symbols typically requires printing a new label to replace the old.

Data carriers such as memory devices provide an alternative method for tracking and providing information about items. Memory devices permit linking of large amounts of data with an object or item. Memory devices typically include a memory and logic in the form of an integrated circuit ("IC") and a mechanism for transmitting data to and/or from the product or item attached to the memory device. A promising memory device-based product identification technology that ameliorates many of the above noted deficiencies of both printed labels and bar coded labels is that of radio frequency identification (RFID) technology. RFID systems use an RF field generator and a plurality of RFID tags attached to goods and products to store and retrieve information about the goods and products. RFID tags are miniature electronic circuits that store identification information about the products they are attached to. An RFID tag typically includes a memory for storing data, an antenna, an RF transmitter, and/or an RF receiver to transmit data, and logic for controlling the various components of the memory device. The basic structure and operation of RFID tags can be found in, for example, U.S. Pat. Nos. 4,075,632, 4,360,801, 4,390,880, 4,739,328 and 5,030,807, the disclosures of which are hereby incorporated by reference in their entirety.

RFID tags generally are formed on a substrate and can include, for example, analog RF circuits and digital logic and memory circuits. The RFID tags also can include a number of discrete components, such as capacitors, transistors, and diodes. The RF transmission of data can be accomplished with modulated back scatter as well as modulation of an active RF transmitter. These RFID tags typically come in one of two types: active or passive. Active tags are characterized in that they have their own power source, such as a battery. When they enter an RF field they are turned on and then emit a signal containing their stored information. Passive tags do not contain a discrete power source. Rather, they become inductively charged when they enter an RF field. Once the RF field has activated the passive circuit, they emit a signal containing their stored information. Passive RFID tags usually include an analog circuit that detects and decodes the interrogating RF signal and that provides power from the RF field to a digital circuit in the tag. The digital circuit generally executes all of the data functions of the RFID tag, such as retrieving stored data from memory and causing the analog circuit to modulate to the RF signal to transmit the retrieved data. In addition to retrieving and transmitting data previously stored in the memory, both passive and active dynamic RFID tags can permit new or additional information to be stored in the RFID tag's memory, or can permit the RFID tag to manipulate data or perform some additional functions.

An advantage of RFID tags over other machine readable ID tags such as bar code tags is that they do not require line of sight to be read by an RFID reader. Because RF waves can penetrate surfaces impervious to light waves, the tags can be encapsulated into ruggedized containers. Furthermore, a group of tags placed within the influence of an RFID reader can be read in batch mode. Also, in the cases of dynamic RFID tags, information stored in the tags can be updated allowing them to serve as transactional records.

Due in part to a relative increase in cost over equivalent bar code-based systems, RFID tags were originally used only on items of sufficiently high value to justify their use or in environments where bar coding was not possible such as anti theft protection. However, with the price of RFID tags now reaching as low as 5 cents per tag, and because of reductions in size due to an overall trend towards miniaturization in circuit designs, they are being applied to many types of products, both at the consumer level as well as in manufacturing processes. RFID tags provide a robust yet cost effective solution to inventory tracking and management.

Other methods of tracking inventory employ color-coding techniques to identify different surgical instruments. Others optically mark each surgical instrument, and later scan the surgical instruments with a hand-held scanner which is connected to a data terminal to ascertain the history of that surgical instrument. These methods require the surgical instrument to be removed from the tray on arrival, and scanned by humans—a method that is costly and time-consuming.

The description herein of various advantages and disadvantages associated with known apparatus, methods, and materials is not intended to limit the scope of the invention to their exclusion. Indeed, various embodiments of the invention may include one or more of the known apparatus, methods, and materials without suffering from their disadvantages.

SUMMARY OF THE INVENTION

There is a need in the art for inventory systems that include a more efficient method and apparatus for acquiring historical data of surgical instruments with speed and efficiency. There also is a need to develop a method and apparatus for acquiring information about surgical instruments that reduces handling costs, automates the verification process, and overcomes some or all of the aforementioned problems.

Embodiments of features of the invention include a method and apparatus for automatically and wirelessly inventorying surgical instruments and the like, by retrieving information indicative of the manufacturer, part number, serial number and manufacturing data, usage and maintenance history of each surgical instrument. The method and apparatus allow for lower handling costs of surgical instruments, increase the accuracy of the verification process of data pertaining to each surgical instrument with a reduction of human contact, and include a real-time data collection resulting in rapid data acquisition, and increased speed of inventory updating of such surgical instruments.

According to a feature of an embodiment of the invention, a radio frequency identification (RFID) reader device is implemented to interrogate a smart surgical instrument tray with a number of surgical instruments that are tagged with a radio frequency identification read/write tags that identify each surgical instrument in terms of manufacturer, part number, name, usage, maintenance history, among other pieces of useful information. In a preferred embodiment, the surgical instrument tray arrives at a distribution center, preferably via a conveyer belt on which the RFID reader of the invention is mounted. As the surgical instrument tray is presented into a wireless radio frequency field of the RFID reader device, an interrogation signal is emitted that activates the RFID tags that are placed on the surgical instruments, and enables a response by the RFID tags via a transceiver/antenna combination. The transceivers along with the antenna collect data from the RFID tagged surgical instruments and passes the data in a wireless or wired fashion to a data output device, such as a desk top PC.

In a preferred embodiment of the present invention, the reader device comprises a power coil that generates power required to power up the radio frequency tags, an antenna connected to a transceiver of the reader device for transmitting interrogation signals, and receiving data signals back from the RFID tags.

Another feature of an embodiment of the invention includes a method and apparatus for identifying surgical instruments in an surgical instrument tray. In this embodiment, outbound surgical instrument trays are packaged together with read/write tags in a warehouse, and inbound surgical instrument trays arriving from customers are received and processed. In a typical embodiment of the invention, a reader device is mounted on a conveyer belt mechanism, or other means for transporting surgical trays, and connected to a host data terminal, preferably a desk-top personal computer. One aspect of the invention provides a smart surgical instrument tray, with its contents of RFID tagged surgical instruments arriving at a central distribution center. The surgical instrument tray is placed on a conveying apparatus, and when the surgical instrument tray reaches a capture zone of reader, the device reader transmits an interrogation signal. In response to the interrogation signal, a transceiver/antenna combination that is incorporated into the surgical instrument tray interrogates the RFID tagged individual surgical instruments, receives a data signal back, and in-turn transfers the data to the reader device. The data then are transferred to a data terminal, or the like, in order to compare the data to a database pertaining to the history of each individual surgical instrument.

Another feature of an embodiment of the invention provides a user-interface application system for facilitating a program that identifies smart trays, and RFID tags that are associated with different surgical instruments. During the creation of a surgical instrument tray and associated RFID-tagged surgical instruments, a user may activate a "Create Tray" field, "Create Instrument" field, and "Associate" field that populates a database on a host data input/output terminal with identification of a tray, the RFID-tagged surgical instruments contained in the tray, and data that associates those tags with a specific tray. On arrival of the surgical instrument trays in the distribution facility, a user may activate a "Verify Tray" field to accurately verify trays and associated surgical instruments, and to check for accuracy of the surgical instrument tray and its contents.

Other aspects and advantages of the invention will become apparent from the following detailed description, taken in conjunction with the accompanying drawings, illustrating by way of example the principles of the invention.

BRIEF DESCRIPTION OF THE DRAWINGS

The purpose and advantages of the present invention will be apparent to those of ordinary skill in the art from the following detailed description in conjunction with the appended drawings in which like reference characters are used to indicate like elements, and in which:

FIG. 6 is an exemplary screen display of the user selection illustrating the tracking of surgical instrument trays, surgical instruments and history according to an embodiment of the present invention.

DETAILED DESCRIPTION OF THE PREFERRED EMBODIMENTS

The following description is intended to convey a thorough understanding of the invention by providing a number of specific embodiments and details involving automating and adding value to surgical instruments, and surgical instrument kits. It is understood, however, that the invention is not limited to these specific embodiments and details, which are exemplary only. It is further understood that one possessing ordinary skill in the art, in light of known systems and methods, would appreciate the use of the invention for its intended purposes and benefits in any number of alternative embodiments, depending upon specific design and other needs.

Preferred embodiments of the present invention include a method and apparatus for automatically and wirelessly inventorying surgical instruments and the like, by retrieving information indicative of the manufacturer, part number, serial number and manufacturing data, cleaning date of each surgical instrument, when the process was completed, etc., and displaying such information on a data output equipment such as a computer. The invention is not limited to the types of information that can be retrieved from the surgical instrument, and skilled artisans will appreciate the various types of useful information that are desirable for each specific instrument. Embodiments of the method and apparatus allow for lower handling costs of surgical instruments, increased accuracy of the verification process of data pertaining to each surgical instrument with a reduction of human contact, and real-time data collection resulting in fast data acquisition that speeds up the inventory updating of such surgical instruments.

Embodiments of the present invention avoid the problems associated with human interaction by implementing an RFID reader that wirelessly acquires data pertaining to each surgical instrument tray and its contents. RFID is a technology that incorporates the use of electromagnetic or electrostatic coupling in the radio frequency (RF) portion of the electromagnetic spectrum to uniquely identify an object, animal, or person. RFID is coming into increasing use in industry as an alternative to the bar code. The advantage of REED is that it does not require direct contact or line-of-sight scanning. An RFID system typically consists of three components: an antenna; a transceiver (often combined with the antenna into one reader); and a transponder (the RF tag) electronically programmed with certain unique information. The antenna emits radio frequency waves to activate the transponder (tag) in order to read or write data to it. In turn, the tag transmits data back to the antenna, data used to interface with a database to carry out a function such as inventory processing.

Figure 1:
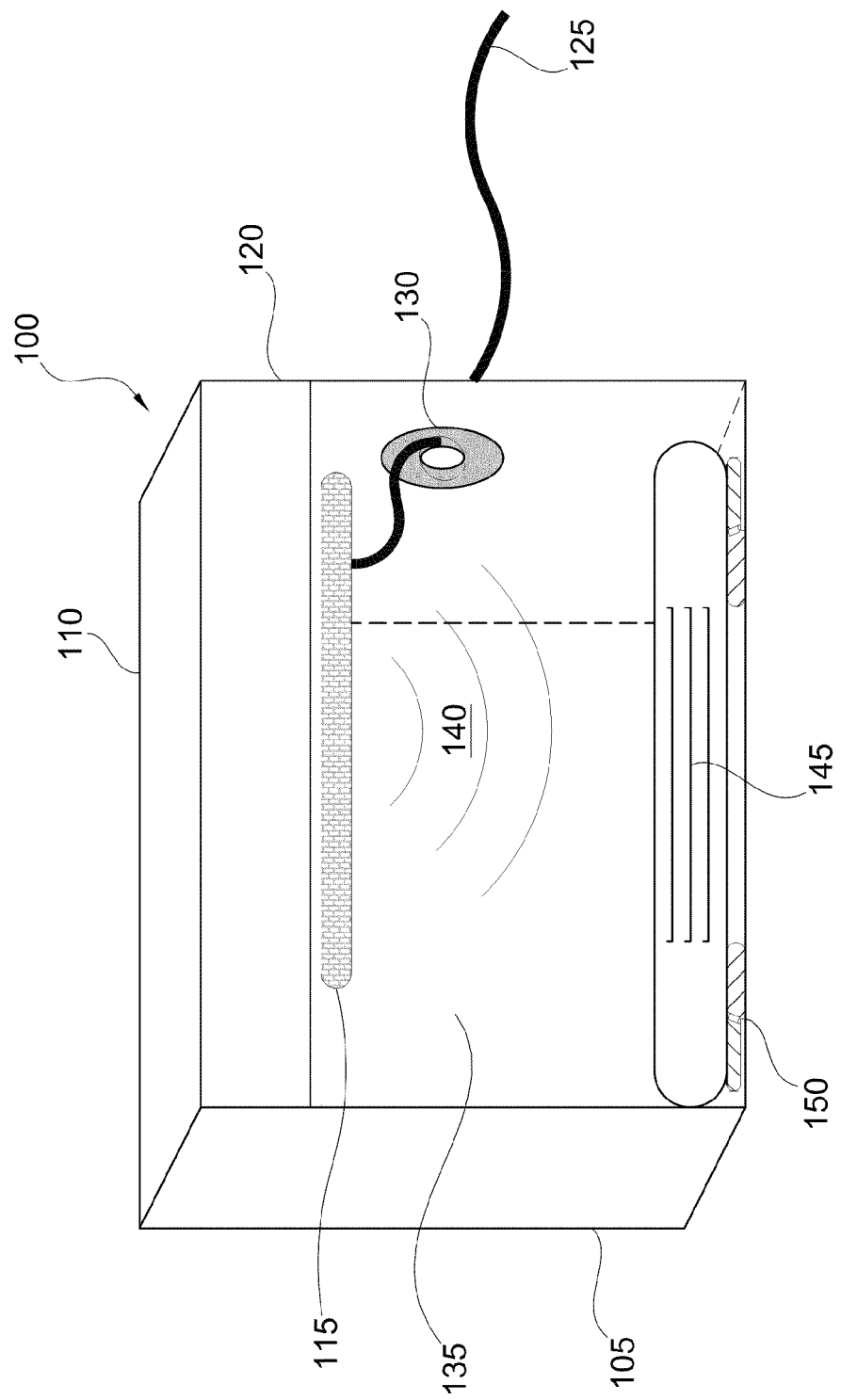
FIG. 1 is a schematic diagram of a radio frequency reader according to an embodiment of the present invention.

Referring to FIG. 1, a radio frequency identification (RFID) reader 100 is illustrated in accordance with one embodiment of the invention. The radio frequency identification (RFID) reader 100 includes side structural members 105, 120 and a top member 110 that reflect electromagnetic waves as a housing for a radio frequency reader situated on a conveyor belt 150. Preferably, these members are made from a metal or other material having structural integrity and capable of reflecting electromagnetic waves. A threaded hole 130 preferably is positioned on one of the side members 105 or 120, to facilitate a cable connection 125 to a data terminal (not shown). An RFID reader module 115, preferably attached to the inside portion of the top member 110, emits a radio frequency signal 140 for interrogating a surgical instrument tray or kit 145, along with the contents of the tray or kit 145, which may include RFID-tagged surgical instruments. It is preferred that the surgical instrument tray or kit 145 passes through a cavity or other aperture 135 created by the structural members of the radio frequency reader 100.

One aspect of this embodiment provides a method whereby: (i) a surgical instrument tray 145, containing a plurality of surgical instruments tagged with read/write RFID tags, arrives at a central distribution center; (ii) an RFID reader 100, positioned on a conveying mechanism 150, preferably a conveyor belt 150, transmits an interrogation signal 140; (iii) in response to the interrogation signal, a transceiver/antenna combination, which preferably is incorporated into the surgical instrument tray 145 and/or on the plurality of RFID tagged surgical instruments, interrogates the RFID tagged components and receives a data signal back; (iv) the transceiver/antenna combination transfers the data to the RFID reader module 115; and (v) the data is transferred to a data terminal via a cable 125 that passes through an opening 130 on the side member 120 of the RFID reader. The data terminal compares the data to information pertaining to the history of each component. Typically, the RFID reader is part of a wireless communication system that includes one more transponders in the form of RFID tags, affixed on surgical instruments to enable the identity of each surgical instrument to be remotely and accurately inspected and verified, as well as each surgical instrument's history of usage, repair and age determined.

In accordance with this embodiment, the RFID reader 100 preferably is either permanently, or temporarily fixed or anchored to the conveying mechanism 150. The instrument tray or kit 145 also preferably includes a plurality of instruments, preferably surgical instruments, that each are individually tagged with an RFID tag. In addition, the cable 125 may pass through opening 130 in any of the members 105, 110, 120, or no cable 125 is employed. In the case of no cable 125, the RFID reader module 115 is capable of wirelessly transmitting data to a data terminal using wireless data transmission techniques well known in the art.

Figure 2:
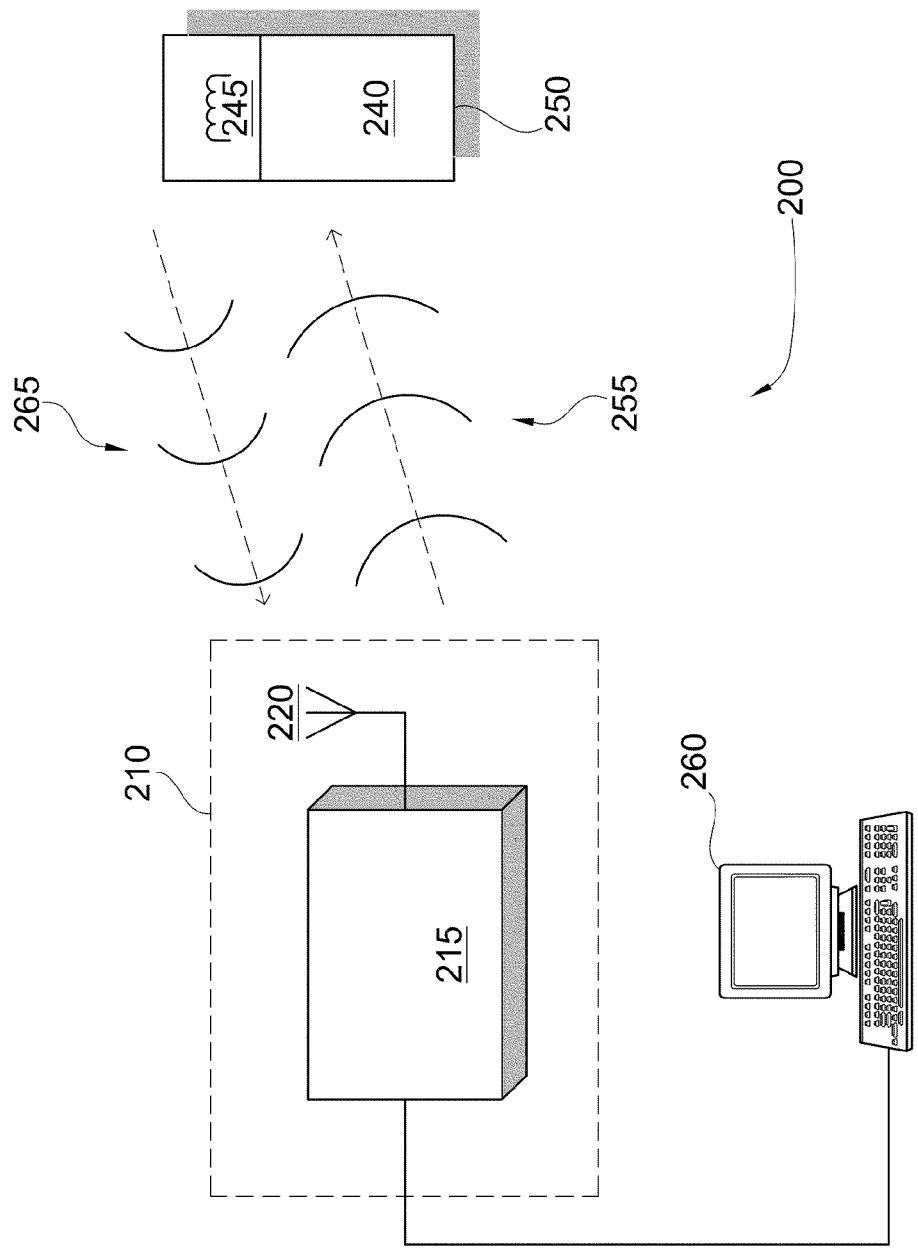
FIG. 2 is a schematic diagram illustration of a wireless radio frequency reader according to an embodiment of the present invention.

According to an additional preferred embodiment of the present invention, and in reference to FIG. 2, the radio frequency identification reader 210 include a transceiver 215 capable of continuously transmitting an interrogation signal 255, in the form of an RF carrier sine wave. The transceiver 215 also is capable of continuously receiving data signals 265, and includes an antenna 220 for transmitting and receiving signals to and from an RFID tagged surgical instrument 250. While the transceiver 215 is capable of continuously transmitting and receiving various signals, skilled artisans will appreciate that the signals need not be continuous, but rather may be initiated by an event, such as the approach of an instrument tray or kit 145 (FIG. 1).

The RFID tag 250 that is affixed to a surgical instrument or other component preferably includes a combined receiving and transmitting antenna/coil 245, preferably a patch antenna for receiving the RF carrier signal 255, and a transceiver 240, which can contain one or more amplifiers, key means, sawtooth pulse generator, a frequency converter, and electronically programmable integrated circuit memory (not shown) for holding data. The integrated circuit memory may be a random access memory (RAM) a memory unit.

The RFID tag being a passive tag can be powered by a rectified AC voltage generated across the antenna coil 245 by the RF field generated by the RFID reader 210. The tag preferably is adapted to deliver stored information to data terminal 260 after modulating the RF carrier transmitted by the RFID reader 210. The storing of information in the memory of the RFID tag can be accomplished in accordance with the procedures set forth in U.S. Pat. No. 4,390,880, the disclosure of which is incorporated by reference herein in its entirety.

For example, a signal 255 (FIG. 2) that is coded, preferably is emitted from reader 210 to the RFID tag transceiver 240. The signal 255 may include a key signal component, which typically is of such a nature that it corresponds to a preselected key code and it actuates a key means that is preferably included in the transceiver 240. The key signal component in turn preferably places the memory in condition for storing coded binary information contained in signal 255 in the form of a pulse train.

More specifically, the RFID reader 210 preferably continuously generates a magnetic alternating field in the radio frequency range, called a carrier signal 255, which activates RFID tag 250 affixed on the surgical instrument or other component when the signal passes through the antenna coil 245. This generates a rectified AC voltage for powering the RFID tag. The activated RFID tag accesses its internal data and sequentially varies the electrical loading of its coil causing slight fluctuation in the RFID reader's carrier signal amplitude, thereby modulating the amount of power drawn by the RFID tag from the reader field. The RFID reader 210 senses the variations in field power consumption corresponding to the data in the RFID tag, and then decodes and outputs the data, which in turn is transmitted to the data terminal 260. This particular method is known in the art as backscatter modulation. Because there may be more than one RFID-tagged surgical instrument in the surgical instrument tray, multiple RFID tags may be read by the reader simultaneously. In order to avoid data corruption due to a number of RFID tags transmitting at the same time, an anti-collision protocol is implemented.

The received, modulated carrier wave 265 at antenna 220 preferably is fed to an envelope detector or the like (which may be a simple rectifying diode) where it is detected (demodulated) to recover or retrieve the modulating signal. The transmitted signal may be made up of two separate signals or signal components that are transmitted one after the other: one being the above-mentioned key signal component; and the other being the information bearing signal component. It is understood that even though the information bearing signal and the key signal are referred to as components of a signal, they are not necessarily modulated onto the radio wave simultaneously, but instead can be transmitted one after another. The key signal component usually immediately precedes the information-bearing signal component in the signal. Each of the key and information-bearing signal components in the signal preferably is advantageously a binary coded digital signal in the form of a pulse train.

Following detection at the transceiver 215, the signal received by the reader device 210 is fed to an amplifier circuit that amplifies the signal. The reader device 210 also preferably includes a decoding mechanism for decoding the coded information in signal. The key means preferably is connected to the output of amplifier circuit to receive the key signal component in signal. The key means can compare the received key signal with a key code that is stored in the key means, and if the received key signal corresponds to the stored key code, the key means operates to feed a write signal to the memory via a conductor or the like. The reader device 210 also preferably includes a voltage controlled oscillator that provides an oscillating output signal frequency, a mixer for downconverting the received signal, one or more bandpass filters, one or more amplifiers, and a demodulator. The write signal preferably places the memory in its write mode and hence in a condition to store incoming data or information. The information-bearing signal or signal component of signal 265 then preferably is fed via a conductor or the like to the data input of the memory and is stored in memory if the received key signal component conforms to the stored key code to cause the generation of the write signal.

The key signal mentioned above preferably is of such a nature to keep reflections from an emitted signal or a signal emitted from an unknown transmitter from placing the memory in its write mode. In this manner, the operation of the key means with the key signal has the effect of avoiding or reducing the chance of storing undesired information in the memory. After storing the information, the key means removes the write signal from the memory so that the memory is rendered incapable, of storing undesirable information. The pulse amplifier (if present), key means and memory are of suitable, known types, and any of the known types or later discovered types can be used in the present invention. The memory capacity in the memory may be, for example, 64 bits or higher. A voltage source, for example a battery with long service life, preferably powers the memory unit so that the information fed into the memory is retained. The data speed of the memory is designed to be sufficient to transfer code depending on the relative speed between the transceiver 215 and the data terminal 260. Those skilled in the art are capable of designing the data speed of the memory depending on the desired relative speeds, using the guidelines provided herein.

Figure 3:
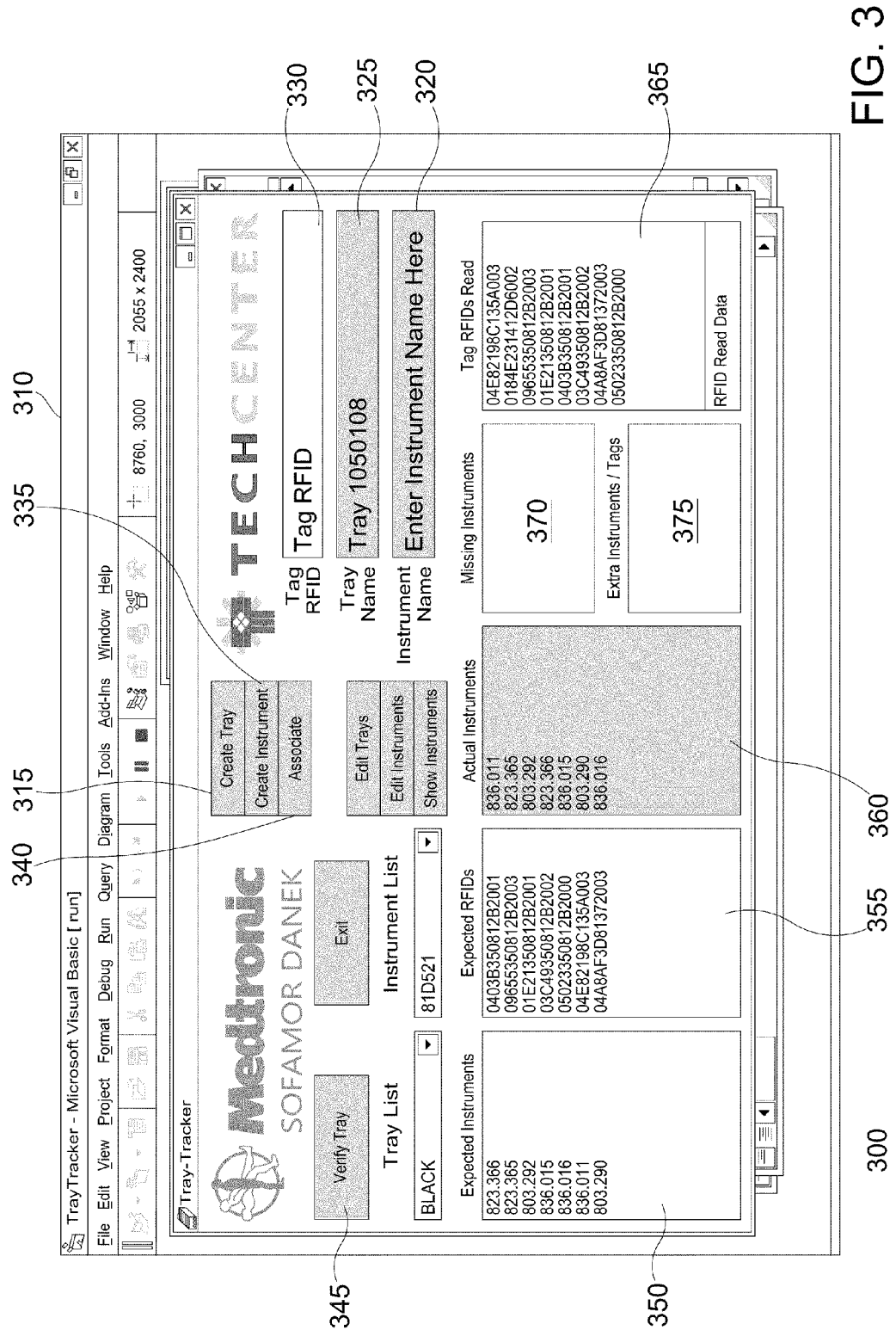
FIG. 3 is an exemplary screen display of the user selection illustrating the tracking of surgical instrument trays according to an embodiment of the present invention.

An additional embodiment of the invention is illustrated in FIG. 3, which is an exemplary screen display associated with a data terminal for identifying and inventorying surgical instruments used in surgical procedures. As shown in FIG. 3, a screen display 310 preferably runs on a custom application program, (although standard application programs also could be used), and comprises a number of fields and user-executable functions. In a preferred embodiment of the present invention, RFID-tagged surgical instruments are packed into individual trays, and before creating an instance of a tray in the database, a user creates an instance of all the RFID-tagged surgical instruments that one particular tray may hold. For example, the user may enter a name for a surgical instrument in the "Instrument Name Field" field 320, and the RFID tag associated with a specific surgical instrument in the "Tag RFID" field 330. The user then may activate the "Create Instrument" field 335, where the application program searches for prior instances of the surgical instrument by checking the entered name or the RFID tag associated with the surgical instrument. The user then is prompted to enter more information, such as the cleaning and sterilizing date of each surgical instrument, whether the process was completed, and other remarks about the instrument. Once the application program verifies that no instances of the surgical instrument exists in the database, the process then moves onto creating the tray in which the RFID-tagged surgical instruments is packaged in.

In a similar fashion, to create an instance of a tray in the database, a user enters a name of a tray in the "Tray Name" field 325, and then activates the "Create Tray" function 315, thereby triggering a database search for any prior instances of the named tray. Once the search is completed, and no prior instances of the of the tray are found, the named surgical instrument in the "Instrument Name" field and the associated RFID tag in the "Tag RFID" field is associated with the tray by activating the "Associate" field 340. Afterwards, the next RFID-tagged surgical instrument is processed and associated with the tray, until the required number of surgical instruments are packaged. The instrument trays, referred to know as "smart" instrument trays, then are shipped back to surgical instrument suppliers, and after their use in surgical operations by hospital personnel, these trays typically are returned to at a distribution center. When a "smart" surgical instrument tray arrives, it can be placed on a conveying mechanism (e.g., a conveyor belt) to pass through a RFID reader of the present invention. The RFID-tagged instruments receive an interrogation signal from the RFID reader, that in turn receives data back, and the received data is transferred to a data terminal.

In an embodiment of the present invention, and in reference to FIG. 3, there is provided a method for verifying the identification of returned surgical instrument trays, and associated surgical instruments. The exemplary screen display of FIG. 3 facilitates a user to run a verification method. On data acquisition from the RFID reader, the user activates the "Verify Tray" field 350 of the screen display associated with a data terminal, which initiates an operation for validating the surgical instrument tray as well as the its contents of RFID-tagged instrument trays against a database containing previously instantiated surgical instrument trays. In response to the activation, the "Expected Instruments" field 360 and the "Expected RFIDs" field 370 are populated with information from the database, while the "Actual Instruments" field 380, and the "Tag RFIDs Read" field 390 are populated with the data read from the smart instrument tray. For faster processing, when there is a match between the data read by the RFID reader and the information in the database, the background of the list in the "Expected Instruments" field 360 turns green for quick visual recognition by the user. In the event that there is a mismatch between the data read by the RFID reader and the information in the database, and there are instruments missing, the "Missing Instrument" field will be populated with a list of the missing instruments, with a red color background to signify an error condition. When the comparison shows more instruments than expected, the "Extra Instruments/Tags" field is populated with a list of the excessive instruments and associated RFID tags, also with a red color background. Skilled artisans will appreciate that any background color can be used, or no background color at all.

Figure 4:
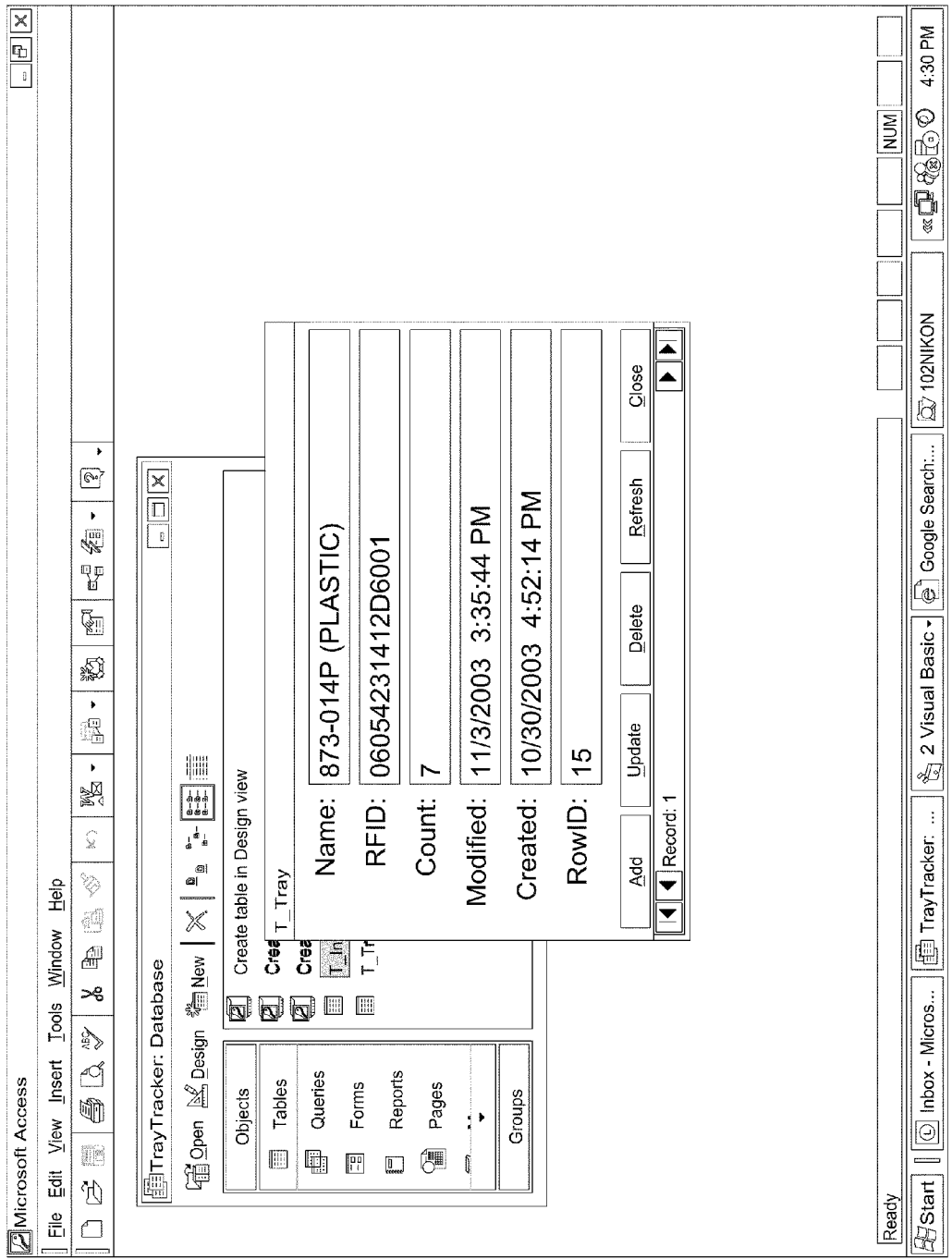
FIG. 4 is an exemplary screen display of the user selection illustrating an surgical instrument tray data table according to an embodiment of the present invention.
Figure 5:
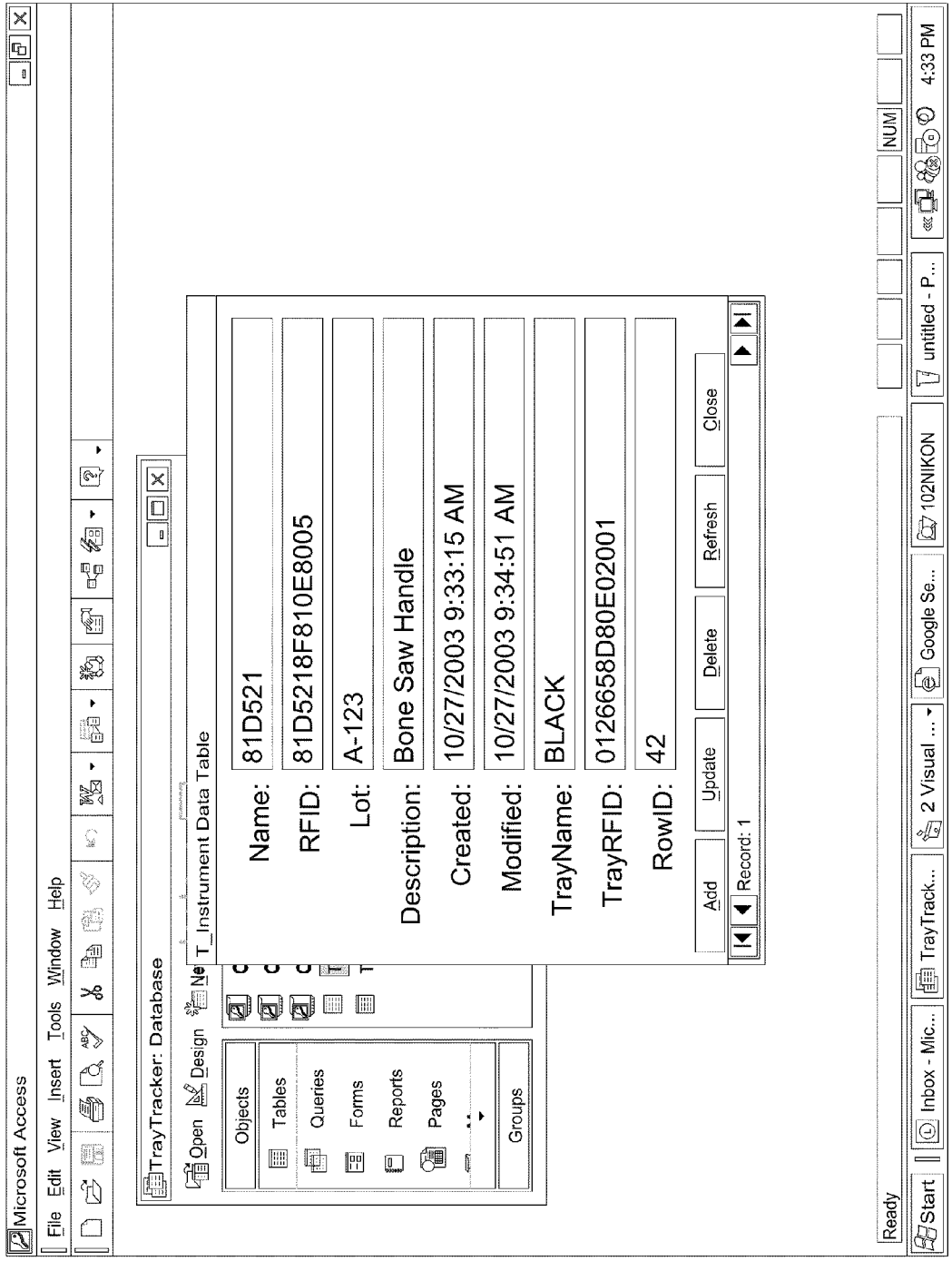
FIG. 5 is an exemplary screen display of the user selection illustrating the creation of surgical instrument trays according to an embodiment of the present invention.
Figure 6:
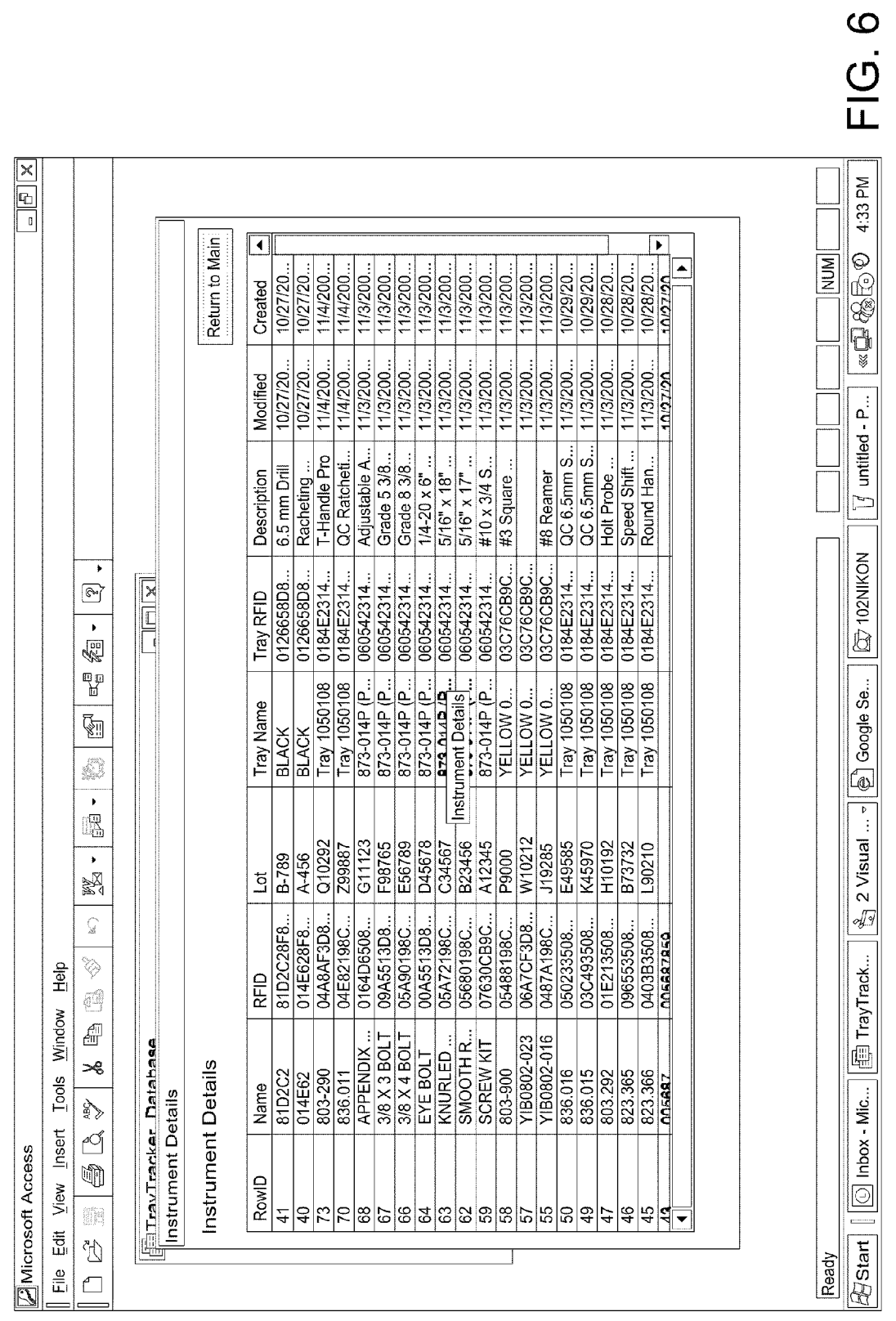

FIGS. 4-6 are various screen displays that could be present using the methods described above with reference to FIG. 3. FIG. 4 depicts a screen display of a surgical instrument tray data table that identifies the instrument tray and its RFID tag number, indicates the number of components (e.g., count 7), and displays when created and last modified. FIG. 5 is a screen display of a particular component in a surgical instrument tray. The display reveals information regarding the component, in this case a bone saw handle, its RFID tag number, the tray it belongs in (and the tray RFID number), as well as when the data was created and last modified. FIG. 6 is a screen display of a table of a variety of surgical instruments, such as all of the instruments tagged by a particular manufacturer. The table can be used to track surgical instrument trays, components of the tray, surgical instruments, and the history of the trays and instruments.

While the foregoing description includes many details and specificities, it is to be understood that these have been included for purposes of explanation only, and are not to be interpreted as limitations of the present invention. Many modifications to the embodiments described above can be made without departing from the spirit and scope of the invention.

What is claimed:

1. A method for verifying contents of a surgical instrument tray, comprising:

moving the tray into a wireless radio frequency (RF) field of an RF reader, the tray provided with an RFID tag, the tray further including a plurality of surgical instruments each tagged with an RFID tag, the surgical instrument RFID tag including instrument data related to the respective surgical instrument, and the tray RFID tag includes data related to the respective surgical instruments contained therein;

receiving at the RF reader an RF signal containing the instrument data from the tagged surgical instruments and an RF signal containing the tray data from the tagged tray to provide read instrument data;

transferring the read instrument data to a terminal connected to the RF reader;

comparing the read instrument data to a database that includes predetermined tray data and surgical instrument data to assess whether the contents of the tray from the read instrument data match the predetermined surgical instrument data in the database; and displaying the read instrument data and the predetermined surgical instrument data.

2. The method of claim 1, further comprising:

detecting a mismatch between the read instrument data and the predetermined surgical instrument data.

3. The method of claim 1, further comprising:

detecting a missing instrument based on comparing the read instrument data and the predetermined surgical instrument data.

4. The method of claim 1, further comprising:

detecting an extra instrument based on comparing the read instrument data and the predetermined surgical instrument data.

5. The method of claim 1, wherein the predetermined surgical instrument data includes usages, age, and repair information for the plurality of tagged surgical instruments.

* * * * *